United States Patent
Stein

(10) Patent No.: US 6,296,944 B1
(45) Date of Patent: Oct. 2, 2001

(54) CURABLE SILICONE ADHESIVE COMPOSITIONS

(75) Inventor: Judith Stein, Schenectady, NY (US)

(73) Assignee: General Electric Company, Schenectady, NY (US)

(*) Notice: Subject to any disclaimer, the term of this patent is extended or adjusted under 35 U.S.C. 154(b) by 0 days.

(21) Appl. No.: 09/539,103

(22) Filed: Mar. 30, 2000

(51) Int. Cl.[7] .................................................. C08G 77/08
(52) U.S. Cl. ........................... 428/447; 528/15; 528/31; 556/440
(58) Field of Search ............................ 556/440; 528/31, 528/15; 428/447

(56) References Cited

U.S. PATENT DOCUMENTS

| 5,164,461 | | 11/1992 | Mitchell et al. ................. 525/478 |
| 5,414,066 | | 5/1995 | Stein et al. ....................... 528/40 |
| 5,550,271 | * | 8/1996 | Stein ................................ 556/440 |
| 6,124,491 | * | 9/2000 | Wolter et al. .................... 556/438 |

* cited by examiner

Primary Examiner—Margaret G. Moore
(74) Attorney, Agent, or Firm—Bernadette M. Bennett; Noreen C. Johnson

(57) ABSTRACT

A silicone composition is provided which comprises a room-temperature vulcanizable adhesive formulation which comprises bis(trialkoxysilylalkyl)hydromuconate.

25 Claims, No Drawings

CURABLE SILICONE ADHESIVE COMPOSITIONS

STATEMENT REGARDING FEDERALLY SPONSORED RESEARCH & DEVELOPMENT

The government has rights in this invention pursuant to Contract No. DAAE3099C1042 awarded by SERDP.

BACKGROUND OF THE INVENTION

The present invention is related to curable silicone compositions. More specifically, the present invention is related to room-temperature vulcanizable adhesive formulations which provide adhesion to substrates.

Curable silicone compositions are used as laminates over a variety of substrates and in a wide variety of applications. In order to impart self-bonding adhesive properties to the silicone composition such that a primer is not needed between the silicone composition and a substrate, adhesion promoters in the silicone composition are commonly used.

Mitchell et al., U.S. Pat. No. 5,164,461, discuss an addition-curable silicone composition which includes a vinyl-containing polydiorganosiloxane, a hydrogen-terminated polysiloxane and an adhesion promoter. The adhesion promoters include silylmaleates, silylmaleimides and silylfumarates. The silicone composition is useful for self-bonding to substrates such as plastics, metals, and glass at a cure temperature in a range between about 100° C. and about 150° C. The silicone composition disclosed has both excellent physical properties and excellent lap shear adhesive properties.

Stein et al., U.S. Pat. No. 5,414,066, is directed to a room-temperature addition-curable silicone adhesive composition which incorporates N-heterocyclic silanes as the adhesion promoter. The addition of the N-heterocyclic silane to a vinyl-containing polydiorganosiloxane and a hydrogen-terminated polysiloxane provides a silicone adhesive composition which cures at room temperature. The composition is directed to providing adhesion to substrates such as glass, plastics and metals.

Although silicone adhesive compositions which have the ability to cure at room temperature has been developed, silicone adhesive compositions with new adhesion promoters are constantly being sought which can both cure at room temperature and include desired physical properties.

BRIEF SUMMARY OF THE INVENTION

The present invention relates to a silicone composition which comprises a room temperature vulcanizable adhesive formulation which comprises at least one bis(trialkoxysilylalkyl)hydromuconate.

A further embodiment of the present invention is a method to provide cohesive failure to a silicone composition and metal substrate which comprises the steps of:

(I) applying a silicone composition to a substrate wherein the silicone composition comprises a bis(trialkoxysilylalkyl)hydromuconate, and (II) curing the silicone composition.

A further embodiment of the present invention provides a bis(trialkoxysilylalkyl)hydromuconate which comprises the formula

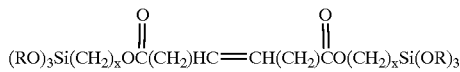

wherein R comprises an alkyl radical, aryl radical, aralkyl radical, alkaryl radical, cycloalkyl radical, or bicycloalkyl radical; and "x" is in a range between about 3 and about 8.

DETAILED DESCRIPTION OF THE INVENTION

It has been found that the incorporation of an effective amount of a bis(trialkoxysilylalkyl)hydromuconate as an adhesion promoter into silicone compositions provides a room-temperature vulcanizable adhesive formulation which adheres to untreated metal substrates. An "effective amount of a bis(trialkoxysilylalkyl)hydromuconate" as used herein is an amount of the adhesion promoter in a range between about 0.1% by weight and about 5% by weight of the total room-temperature vulcanizable adhesive formulation, herein referred to as "total composition".

The adhesion promoter is at least one bis(trialkoxysilylalkyl)hydromuconate which has the general formula (I):

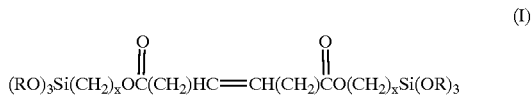

wherein "x" has a value in a range between about 3 and about 8. Each R independently represents a monovalent hydrocarbon group such as alkyl radicals, aryl radicals, aralkyl radicals, alkaryl radicals, cycloalkyl radicals, or bicycloalkyl radicals. The term "alkyl radical" is intended to designate both normal alkyl and branched alkyl radicals. Normal and branched alkyl radicals are preferably those containing carbon atoms in a range between about 1 and about 20, and include as illustrative non-limiting examples methyl, ethyl, propyl, isopropyl, butyl, tertiary-butyl, pentyl, neopentyl, hexyl, octyl, decyl, dodecyl. Aryl radicals include examples such as phenyl and tolyl. Cyclo- or bicycloalkyl radicals represented are preferably those containing ring carbon atoms in a range between about 3 and about 12 with a total number of ring carbon atoms less than or equal to about 50. Some illustrative non-limiting examples of these cycloalkyl radicals include cyclobutyl, cyclopentyl, cyclohexyl, methylcyclohexyl, and cycloheptyl. Preferred aralkyl radicals are those containing carbon atoms in a range between about 7 and about 14; these include, but are not limited to, benzyl, phenylbutyl, phenylpropyl, and phenylethyl. Most preferably, a bis(trimethoxysilylpropyl)hydromuconate is used as the adhesion promoter wherein R comprises an alkyl radical with 1 carbon atom and "x" is 3.

The bis(trialkoxysilylalkyl)hydromuconate can be synthesized by first synthesizing an allyl ester by effecting a reaction between hydromuconic acid, a thionyl halide, such as thionyl chloride, and dimethylformamide. The resulting allyl ester can be reacted with trialkoxysilane using a hydrosilylation catalyst, for example, a platinum catalyst to form the bis(trialkoxysilylalkyl)hydromuconate.

In addition to the effective amount of at least one bis(trialkoxysilylalkyl)hydromuconate, the room-temperature vulcanizable adhesive formulation includes (A) a vinyl-containing polydiorganosiloxane present in a range between about 10% by weight and about 50% by weight of the total composition, (B) a hydrogen-containing polysiloxane in a range between about 1% by weight and about 15% by weight of the total composition, (C) a catalytic amount of a hydrosilylation catalyst of at least about 0.1 part per million, (D) an extending filler in a range between about 0% by weight and about 50% by weight of the total composition, and (E) a reinforcing filler in a range between about 0% by weight and about 70% by weight of the total composition.

The vinyl-containing polydiorganosiloxane (A) includes (1) a vinyl-containing polydiorganosiloxane and optionally, (2) a vinyl-containing siloxane resin copolymer.

The vinyl-containing polydiorganosiloxane has the general formula (II),

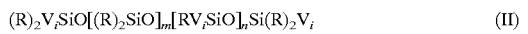

(R)$_2$V$_i$SiO[(R)$_2$SiO]$_m$[RV$_i$SiO]$_n$Si(R)$_2$V$_i$     (II)

wherein "V$_i$" is a vinyl radical, "R" is selected from the group consisting of C$_{1-8}$ alkyl radicals, phenyl radicals, and C$_{3-10}$ fluoroalkyl radicals and mixtures thereof, "m"+"n" has a value sufficient to provide a total vinyl-containing composition with a viscosity in a range between about 100 centipoise and about 100,000 centipoise at 25° C., and preferably, in a range between about 3000 centipoise and about 95,000 centipoise at 25° C. and a vinyl content in a range between about 0.02% by weight and about 2.0% by weight of the vinyl-containing polydiorganosiloxane. Radicals represented by "R" are preferably C$_{1-4}$alkyl radicals and more preferably, methyl.

The vinyl-containing siloxane resin copolymer is present in a range between about 0% by weight and about 70% by weight of the total composition comprising,

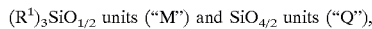

(R$^1$)$_3$SiO$_{1/2}$ units ("M") and SiO$_{4/2}$ units ("Q"), wherein "R$^1$" is a vinyl radical, or a monovalent hydrocarbon radical free of aliphatic unsaturation and containing no more than six carbon atoms, the ratio of (R$^1$)$_3$SiO$_{1/2}$ units to SiO$_{4/2}$ units being in a range between about 0.5:1 and about 1.5:1, and the resin having a vinyl content in a range between about 1.5% by weight and about 3.5% by weight of the vinyl-containing siloxane resin copolymer. The vinyl-containing siloxane resin copolymer is also referred to as the "vinyl-containing MQ resin" or "M$^{Vi}$Q".

The vinyl-containing siloxane resin copolymer may further contain (i) R$^1$SiO$_{3/2}$ units, (ii) (R$^1$)$_2$SiO$_{2/2}$ units, or combinations thereof, where the (R$^1$)$_2$SiO$_{2/2}$ units are present in an amount in a range between about 0 mole percent and about 10 mole percent based on the total number of moles of siloxane units in the vinyl-containing siloxane resin copolymer and "R$^1$" is as defined above.

The hydrogen-containing polysiloxane (B) functions as a cross-linking agent. The hydrogen-containing polysiloxane is represented by an average unit formula (III),

R$^2_d$H$_e$SiO$_{(4-d-e)/2}$     (III)

wherein "R$^2$" is hydrogen, a monovalent hydrocarbon radical, or halogenated monovalent hydrocarbon radical having in a range between 1 and 10 carbon atoms, and free of aliphatic unsaturation, "d" has a value in a range between 0 and 3, "e" has a value in a range between 1 and 3, and the sum of "d"+"e" has a value in a range between 1 and 3.

A preferred hydrogen-containing polysiloxane has the formula (IV)

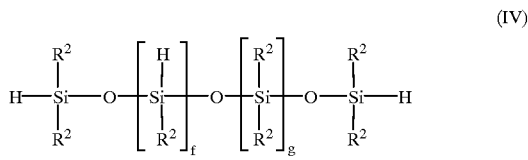

(IV)

where "R$^2$" is as defined above, "f" and "g" have values which are sufficient when added together to provide a viscosity in a range between about 10 centipoise and about 1000 centipoise, and preferably, in a range between about 10 centipoise and about 150 centipoise at 25° C., and the reactive hydrogen content is in a range between about 0.02% by weight and about 1.6% by weight of the hydrogen-containing polysiloxane.

The hydrogen-containing polysiloxane of formula (IV) can be used as a hydride cross-linking agent in the present invention. In formulas (III) and (IV) above, "R$^2$" is preferably selected from C$_{1-8}$ alkyl radicals, phenyl, C$_{3-10}$ fluoroalkyl radicals, and hydrogen. Most typically, the preferred fluoroalkyl radical is trifluoropropyl.

Other hydrogen-containing polysiloxanes which can be used in the present invention include siloxane copolymer resins comprised of "M" units which comprise (R$^2$)$_3$SiO$_{1/2}$, "M$^H$" units which comprise H(R$^2$)$_2$SiO$_{1/2}$, "D" units which comprise (R$^2$)$_2$SiO$_{2/2}$, "D$^H$" units which comprise HR$^2$SiO$_{2/2}$, "T" units which comprise (R$^2$)SiO$_{3/2}$, "T$^H$" units which comprise HSiO$_{3/2}$, and "Q" units which comprise SiO$_{4/2}$, and mixtures thereof wherein the mixtures comprise at least one hydrogen. The preferred resins are known as M$^H$Q resins, which comprise diorganohydrogensiloxy units (M$^H$) and SiO$_{4/2}$ units (Q) wherein the ratio of diorganohydrogensiloxy units to Q units is in a range between about 0.4:1.0 and about 2.0:1.0 inclusive. Hydrogen-containing polysiloxanes having at least one R$^2$ group, preferably, a methyl group, bonded to silicon which bears at least one reactive hydrogen atom are preferred. It is understood that the hydrogen-containing polysiloxane can be a single compound or a mixture of compounds. Additional hydrogen-containing polysiloxanes suitable for use in the present invention are described, for example, in U.S. Pat. No. 4,061,609.

The room-temperature vulcanizable adhesive formulation further contains a catalytic amount of a hydrosilylation catalyst (C). The hydrosilylation catalyst (C) promotes the hydrosilylation reaction. The hydrosilylation catalyst (C) typically is a platinum group metal catalyst. Additional catalysts for facilitating the hydrosilylation curing reaction include precious metal catalysts such as those containing ruthenium, rhodium, palladium, osmium, or iridium, or complexes of these metals. Examples of suitable hydrosilylation catalysts for use in the present invention are disclosed, for example, in U.S. Pat. Nos. 3,159,601 and 3,159,662; 3,220,970; 3,814,730; 3,516,946; and 4,029,629.

The hydrosilylation catalyst is preferably a platinum containing catalyst. Preferably, the platinum-containing catalyst is a platinum complex formed by reacting chloroplatinic acid containing about 4 moles of water of hydration with tetravinylcyclotetrasiloxane in the presence of sodium bicarbonate in an ethanol solution. This catalyst is disclosed in U.S. Pat. No. 3,775,452 and is often referred to as Karstedt's catalyst.

The hydrosilylation catalyst is used in a catalytic amount, which is an amount sufficient to promote the hydrosilylation reaction. Generally, there must be utilized at least about 0.1 part per million of a platinum catalyst, and preferably in a range between about 5 parts per million and about 250 parts per million, in terms of parts of platinum metal based on the weight of total composition. Inhibitors such as acetylenic alcohols, amines, cyanurates, $D_4^{Vi}$ (e.g., 3,5 dimethyl-1-hexyn-3-ol and 2 methyl-3-butyn-2-ol) and mixtures thereof can also be employed when used in an effective amount which is typically in a range between about 0.01% by weight and about 1% by weight of the total composition.

The room-temperature vulcanizable adhesive formulation of the present invention may also contain any of the conventional extending fillers (D), reinforcing fillers (E), and mixtures thereof. The room-temperature vulcanizable adhesive formulation contains extending filler in a range between about 0% by weight and about 50% by weight, and preferably in a range between about 10% by weight and about 30% by weight of the total composition, and reinforcing filler in a range between about 0% by weight and about 70% by weight, and preferably in a range between about 20% by weight and about 50% by weight of the total composition.

Examples of extending fillers (D) useful herein include alpha quartz, crushed quartz, aluminum oxide, aluminum silicate, zirconium silicate, magnesium oxide, zinc oxide, talc, diatomaceous earth, iron oxide, calcium carbonate, clay, titania, zirconia, mica, glass, such as ground glass or glass fiber, sand, carbon black, graphite, barium sulfate, zinc sulfate, wood flour, cork, fluorocarbon polymer powder and the like. Alpha quartz is the most preferred extending filler.

Examples of reinforcing fillers (E) include silica, such as fumed silica or precipitated silica, and treated silica fillers such as fumed or precipitated silica that has been reacted with, for example, an organohalosilane, a disiloxane, or a disilazane. Fumed silica is particularly effective as a reinforcing filler for the compositions of the present invention. A particularly preferred treated fumed silica is one wherein the fumed silica has been treated first with cyclic polysiloxanes, for example, dimethylcyclic tetramer, according to the methods as described in U.S. Pat. No. 2,938,009, and then treated with a silazane, for example, hexamethyldisilazane, as described in U.S. Pat. Nos. 3,635,743 and 3,847,848 so as to remove most of the free silanols on the surface of the tetramer treated silica. Removal of most of the free silanols refers to less than about 30% silanols remaining on the surface of the tetramer treated silica. Such a filler is sometimes referred to herein as "treated fumed silica".

The room-temperature vulcanizable adhesive formulation of the present invention typically is prepared by homogeneously mixing (i.e. uniformly mixing) components (A)–(D) with the adhesion promoter and any optional ingredients, using suitable batch, continuous, or semi-continuous mixing means, such as a spatula, a drum roller, a mechanical stirrer, a three-roll mill, a sigma blade mixer, a bread dough mixer, or a two-roll mill.

It is possible to mix all components in one mixing step immediately prior to the intended use of the curable composition. Alternatively, certain components can be premixed to form two or more packages which can be stored, if desired, and then mixed in a final step immediately prior to the intended use thereof.

Preferably, the vinyl-containing polydiorganosiloxane (A) will be homogeneously mixed with a hydrosilylation catalyst and any additional reinforcing filler to form a package (1). Package (2) will be a mixture of the hydrogen-containing polysiloxane (B), at least one vinyl-containing polydiorganosiloxane, and inhibitor. Package (2) is modified with adhesion promoter, additional inhibitor, and additional hydrogen-containing polysiloxane. Package (1) and package (2) are then homogeneously mixed. Typically, the weight ratio of package (1) to package (2) is in a range between about 15:1 and about 1:1 and preferably, in a range between about 12:1 and about 1:1. These two packages can then be stored until the composition of this invention is desired and then homogeneously mixed.

The thickness of the total composition on a substrate is typically in a range between about 20 millimeters and about 60 millimeters. The total composition of the present invention can be applied to the surface of a substrate by any suitable means such as rolling, spreading, spraying, and the like, and cured. After application of the total composition onto the substrate, the composition can be cured at room temperature over a period in a range between about 0.25 hours and about 150 hours. Typically, the cure temperature is in a range between about 25° C. and about 150° C.

The total composition, when applied to a substrate, of the present invention has the desirable property of failing cohesively instead of adhesively when tested. A lap shear adhesion strength test is commonly used to measure adhesive failure and cohesive failure. "Adhesive failure" as used herein indicates that the silicone layer separates from the substrate at the point wherein the two layers meet, that is, the bond between the silicone layer and the substrate ruptures before the silicone layer of the substrate ruptures. "Cohesive failure" as used herein indicates that the silicone layer or the substrate ruptures before the bond between the silicone layer and the substrate fails.

The room-temperature vulcanizable adhesive formulation has been found to cohesively bond on untreated and treated metal substrates. Treating the metal substrate may include cleaning the substrate, applying a primer known to those skilled in the art, or a combination thereof. Preferably, the room-temperature vulcanizable adhesive formulation is used on untreated and treated aluminum-clad substrates. Most preferably, the room-temperature vulcanizable adhesive formulation is used on untreated aluminum-clad substrates. The compositions can be used as adhesives for applications in the military and laser industry as well as the electronic industry and automotive industry.

Room-temperature vulcanizable adhesive formulations cure by mechanisms such as hydrosilylation or condensation. In order that those skilled in the art may better understand the practice of the present invention, the following examples of silicone compositions curing via hydrosilylation are given by way of illustration and not by way of limitation.

EXAMPLE 1

A 25 milliliter round-bottom flask was equipped with a reflux condenser, a stir bar, a nitrogen inlet, and charged with 5 grams hydromuconic acid (36 millimoles), 16 grams of thionyl chloride, and 0.1 grams of dimethylformamide. The mixture was heated at 40° C. for three hours at which time it had become homogenous. The excess thionyl chloride was distilled off and excess allyl alcohol (30 milliliters) was added. The mixture was stirred overnight. The product was isolated by vacuum distillation at 135° C. To 2.0 grams of the purified allyl ester was added 25 microliters of Karstedt's catalyst and the mixture was heated to 100° C. After reaching temperature, 2.5 grams of trimethoxysilane was added dropwise over a period of approximately 15 minutes. The reaction was complete after heating overnight. The purity and identity of the product were determined by gas chromatography and proton nuclear magnetic resonance spectroscopy as bis(trimethoxysilylpropyl)hydromuconate.

A silicone composition was prepared by adding 0.15 grams of $M^H{}_2Q$ resin and 0.22 grams of bis (trimethoxysilylpropyl)-hydromuconate to modify 2 grams of package (2). Package (2) initially contained 47.5% by weight of a vinyl-terminated polydimethylsiloxane (0.06% by weight vinyl content; viscosity of 78,000 centipoise), 47.5% of a hydrogen-containing siloxane (0.8% by weight hydride content; viscosity of 40 centipoise), 3.8% by weight of methylvinyl tetramer inhibitor, and 0.1% by weight of 3,5 dimethyl-1-hexyn-3-ol inhibitor. The modified package (2) was then combined with 20 grams of package (1) which contained 30 ppm of platinum catalyst, 40.4% of a silicone resin (1.26% by weight vinyl content; viscosity of 32,000 centipoise), 20.3% of a vinyl-terminated polydimethylsiloxane (0.06% by weight vinyl content; viscosity of 78,000 centipoise), 12% of a vinyl-terminated polydimethylsiloxane (0.17% by weight vinyl content; viscosity of 3,700 centipoise), and 27.6% silica filler. The modified package (2) and package (1) were mixed thoroughly and degassed under vacuum to provide a room-temperature vulcanizable adhesive formulation. The room-temperature vulcanizable adhesive formulation was applied to aluminum clad/aluminum clad lap shear samples (one inch by four inches) with a one inch overlap. The specimens were cured at 50° C. for one hour or 7 days at room temperature. The lap shear adhesion strength was measured on an Instron 4202 instrument with a crosshead speed of 2 inches per minutes. The room-temperature vulcanizable adhesive formulation with bis (trimethoxysilylpropyl)hydromuconate as the adhesion promoter was compared to a room-temperature vulcanizable formulation with bis(trimethoxysilylpropyl)fumarate (1% by weight of the total composition), hereinafter referred to as "fumarate", as the adhesion promoter and a room-temperature vulcanizable formulation without an adhesion promoter. The results can be seen in Table 1.

TABLE 1

| Adhesion Promoter | Cure Conditions | Failure Mode | Lapshear Strength (psi) |
|---|---|---|---|
| Example 1 | 50° C./4 hours | 90–100% cohesive | 674 +/– 18 |
| Example 1 | Room temperature/7 days | 90–100% cohesive | 500 +/– 52 |
| Fumarate | 70° C./4 hours | Did not cure | |
| None | 100° C./1 hour | 100° adhesive | 3 |

EXAMPLES 2–11

Compositions were made by the method of Example 1 with varying amounts of bis(trimethoxysilylpropyl)hydromuconate, additional hydrogen-containing polysiloxane, and inhibitor. Aluminum clad/aluminum clad lap shear samples (one inch by four inches) were prepared with a one inch overlap. The specimens were cured at room temperature for 6 days. The lap shear adhesion strength was measured on an Instron 4202 instrument with a crosshead speed of 2 inches per minutes. The compositions and test results are seen in Table 2.

TABLE 2

| Sample | Adhesion promoter (g) | Silicone hydride (g) | Inhibitor (μl) | Failure Mode | Lapshear Strength (psi) |
|---|---|---|---|---|---|
| 2 | 0.17 | 0.00 | 5 | 100% cohesive | 650 +/– 19 |
| 3 | 0.17 | 0.15 | 5 | 100% cohesive | 513 +/– 28 |
| 4 | 0.17 | 0.00 | 2.5 | 100% cohesive | 606 +/– 29 |
| 5 | 0.27 | 0.00 | 2.5 | 100% cohesive | 543 +/– 49 |
| 6 | 0.27 | 0.15 | 2.5 | 100% cohesive | 510 +/– 27 |
| 7 | 0.27 | 0.15 | 5 | 100% cohesive | 582 +/– 39 |
| 8 | 0.27 | 0.00 | 5 | 100% cohesive | 687 +/– 45 |
| 9 | 0.17 | 0.15 | 2.5 | 100% cohesive | 678 +/– 78 |
| 10 | 0.22 | 0.075 | 3.75 | 100% cohesive | 607 +/– 26 |
| 11 | 0.22 | 0.075 | 3.75 | 100% cohesive | 637 +/– 33 |

The results indicated that bis(trimethoxysilylpropyl) hydromuconate is an effective adhesion promoter when incorporated into silicone compositions. Compositions with the bis(trimethoxysilylpropyl)hydromuconate additive are capable of curing at room temperature and lap shear composites fail cohesively within the silicone.

While typical embodiments have been set forth for the purpose of illustration, the foregoing descriptions should not be deemed to be a limitation on the scope of the invention. Accordingly, various modifications, adaptations, and alternatives may occur to one skilled in the art without departing from the spirit and scope of the present invention.

What is claimed is:

1. A silicone composition comprising a room-temperature vulcanizable adhesive formulation which comprises at least one bis(trialkoxysilylalkyl)hydromuconate.

2. The composition in accordance with claim 1, wherein the room-temperature vulcanizable adhesive formulation further comprises
   (A) a vinyl-containing polydiorganosiloxane present in a range between about 10% by weight and about 50% by weight of the total composition,
   (B) a hydrogen-containing polysiloxane in a range between about 1% by weight and about 15% by weight of the total composition,
   (C) a catalytic amount of a hydrosilylation catalyst,
   (D) an extending filler in a range between about 0% by weight and about 50% by weight of the total composition, and
   (E) a reinforcing filler in a range between about 0% by weight and about 70% by weight of the total composition.

3. The composition in accordance with claim 2, wherein the vinyl-containing polydiorganosiloxane comprises a vinyl-containing polydiorganosiloxane having a general formula,

$(R)_2V_iSiO[(R)_2SiO]_m[RV_iSiO]_nSi(R)_2V_i$ wherein $V_i$ is a vinyl radical, R is selected from the group consisting of alkyl radicals having in a range between 1 and 9 carbon atoms, phenyl radicals, fluoroalkyl radicals, having in a range between about 3 and 10 carbon atoms and mixtures thereof, "m"+"n" has a value sufficient to provide a total polydiorganosiloxane viscosity in a range between about 100 centipoise and about 100,000 centipoise at 25° C., and a vinyl content in a range between about 0.02% by weight and about 2.0% by weight of the vinyl-containing polydiorganosiloxane, and a vinyl-containing silicone resin copolymer in a range between about 0% by weight and about 70% by weight of the total composition having, $(R^1)_3SiO_{1/2}$ units and $SiO_{4/2}$ units, wherein $R^1$ is a vinyl radical, or a monovalent hydrocarbon radical free of aliphatic unsaturation and containing no more than six carbon atoms, the ratio of $(R^1)_3SiO_{1/2}$ units to $SiO_{4/2}$ units being in a range between about 0.5:1 and about 1.5:1, and the resin having a vinyl content in a range between about 1.5% by weight and about 3.5% by weight of the vinyl-containing siloxane resin copolymer.

4. The composition in accordance with claim 2, wherein the hydrogen-containing polysiloxane comprises units of the formula, $$R^2_dH_eSiO_{(4-d-e)/2}$$

wherein $R^2$ is a hydrogen, a monovalent hydrocarbon radical, or a halogenated monovalent hydrocarbon radical having in a range between 1 and 10 carbon atoms, and free of aliphatic unsaturation, "d" has a value in a range between 0 and 3, "e" has a value in a range between 1 and 3, and the sum of "d"+"e" has a value in a range between 1 and 3.

5. The composition in accordance with claim 1, wherein the bis(trialkoxysilylalkyl)hydromuconate has a formula

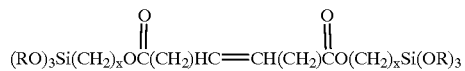

wherein each R independently represents an alkyl radical comprising carbon atoms in a range between about 1 and about 20; and "x" is in a range between about 3 and about 8.

6. The composition in accordance with claim 5, wherein the bis(trialkoxysilylalkyl)hydromuconate comprises bis(trimethoxysilylpropyl)-hydromuconate.

7. The composition in accordance with claim 1, wherein the bis(trialkoxysilylalkyl)hydromuconate is present in a range between about 0.1% by weight and about 5% by weight of the total composition.

8. The composition in accordance with claim 1, wherein the composition promotes adhesion to metal substrates.

9. The composition in accordance with claim 8, wherein the substrate comprises aluminum.

10. A metal substrate treated with the composition of claim 1.

11. The substrate in accordance with claim 10, wherein the substrate comprises aluminum.

12. A silicone composition comprising a room-temperature vulcanizable adhesive formulation which promotes adhesion to metal substrates, which composition comprises (F) at least one bis(trimethoxysilylpropyl)hydromuconate present in a range between about 0.1% by weight and about 5% by weight of the total composition;

(G) a vinyl-containing polydiorganosiloxane present in a range between about 10% by weight and about 50% by weight of the total composition, (H) a hydrogen-containing polysiloxane in a range between about 1% by weight and about 15% by weight of the total composition, (I) a catalytic amount of a hydrosilylation catalyst, (J) an extending filler in a range between about 0% by weight and about 50% by weight of the total composition, (K) a reinforcing filler in a range between about 0% by weight and about 70% by weight of the total composition.

13. A metal substrate treated with the composition of claim 12.

14. The substrate in accordance with claim 13, wherein the substrate comprises aluminum.

15. A method to provide cohesive failure to a silicone composition and metal substrate which comprises the steps of:

(I) applying a silicone composition to a substrate wherein the silicone composition comprises at least one bis(trialkoxysilylalkyl)hydromuconate, and (II) curing the silicone composition.

16. The method in accordance with claim 15, wherein the silicone composition further comprises (L) a vinyl-containing polydiorganosiloxane present in a range between about 10% by weight and about 50% by weight of the total composition, (M) a hydrogen-containing polysiloxane in a range between about 1% by weight and about 15% by weight of the total composition, (N) a catalytic amount of a hydrosilylation catalyst, (O) an extending filler in a range between about 0% by weight and about 50% by weight of the total composition, and (P) a reinforcing filler in a range between about 0% by weight and about 70% by weight of the total composition.

17. The method in accordance with claim 16, wherein the vinyl-containing polydiorganosiloxane comprises a vinyl-containing polydiorganosiloxane having a general formula, $$(R)_2V_iSiO[(R)_2SiO]_m[RV_iSiO]_nSi(R)_2V_i$$

wherein $V_i$ is a vinyl radical, R is selected from the group consisting of alkyl radicals having in a range between 1 and 9 carbon atoms, phenyl radicals, fluoroalkyl radicals, having in a range between about 3 and 10 carbon atoms and mixtures thereof, "m"+"n" has a value sufficient to provide a total polydiorganosiloxane viscosity in a range between about 100 centipoise and about 100,000 centipoise at 25° C., and a vinyl content in a range between about 0.02% by weight and about 2.0% by weight of the vinyl-containing polydiorganosiloxane, and a vinyl-containing silicone resin copolymer in a range between about 0% by weight and about 70% by weight of the total composition having, $(R^1)_3SiO_{1/2}$ units and $SiO_{4/2}$ units, wherein $R^1$ is a vinyl radical, or a monovalent hydrocarbon radical free of aliphatic unsaturation and containing no more than six carbon atoms, the ratio of $(R^1)_3SiO_{1/2}$ units to $SiO_{4/2}$ units being in a range between about 0.5:1 and about 1.5:1, and the resin having a vinyl content in a range between about 1.5% by weight and about 3.5% by weight of the vinyl-containing siloxane resin copolymer.

18. The composition in accordance with claim 16, wherein the hydrogen-containing polysiloxane comprises an average unit formula, $$R^2_dH_eSiO_{(4-d-e)/2}$$

wherein $R^2$ is a hydrogen, a monovalent hydrocarbon radical, or a halogenated monovalent hydrocarbon radical having in a range between 1 and 10 carbon atoms, and free of aliphatic unsaturation, "d" has a value in a range between 0 and 3, "e" has a value in a range between 1 and 3, and the sum of "d"+"e" has a value in a range between 1 and 3.

19. The method in accordance with claim 15, wherein the bis(trialkoxysilylalkyl)hydromuconate has a formula

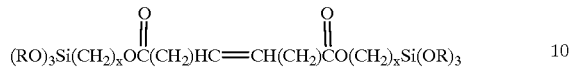

wherein each R independently represents an alkyl radical comprising carbon atoms in a range between about 1 and about 20; and "x" is in a range between about 3 and about 8.

20. The method in accordance with claim 19, wherein the bis(trialkoxysilylalkyl)hydromuconate comprises bis(trimethoxysilylpropyl)-hydromuconate.

21. The method in accordance with claim 15, wherein the bis(trialkoxysilylalkyl)hydromuconate is present in a range between about 0.1% by weight and about 5% by weight of the total composition.

22. The method in accordance with claim 15, wherein the metal substrate comprises aluminum.

23. The method in accordance with claim 15, wherein the silicone composition is applied to a thickness in a range between about 20 millimeters and about 60 millimeters.

24. The method in accordance with claim 15, wherein the silicone composition is cured at a temperature in a range between about 25° C. and about 150° C. over a period in a range between about 0.25 hours and about 150 hours.

25. A method to provide cohesive failure to a silicone composition and an aluminum clad substrate which comprises the steps of:

(1) applying a silicone composition to a substrate to a thickness in a range between about 20 millimeters and about 60 millimeters, wherein the silicone composition comprises (I) bis(trimethoxysilylpropyl)hydromuconate present in a range between about 0.1% by weight and about 5% by weight of the total composition;

(J) a vinyl-containing polydiorganosiloxane present in a range between about 10% by weight and about 50% by weight of the total composition, (K) a hydrogen-containing polysiloxane in a range between about 1% by weight and about 15% by weight of the total composition, (L) a catalytic amount of a hydrosilylation catalyst, (M) an extending filler in a range between about 0% by weight and about 50% by weight of the total composition, (N) a reinforcing filler in a range between about 0% by weight and about 70% by weight of the total composition, and (2) curing the silicone composition at a temperature in a range between about 25° C. and about 150° C. over a period in a range between about 0.25 hours and about 150 hours.

* * * * *